United States Patent
Metcalf et al.

(10) Patent No.: US 9,622,811 B2
(45) Date of Patent: Apr. 18, 2017

(54) SURGICAL INSTRUMENT AND METHOD

(71) Applicant: Warsaw Orthopedic, Inc., Warsaw, IN (US)

(72) Inventors: Newton H. Metcalf, Memphis, TN (US); Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 209 days.

(21) Appl. No.: 14/186,019

(22) Filed: Feb. 21, 2014

(65) Prior Publication Data

US 2015/0238246 A1     Aug. 27, 2015

(51) Int. Cl.
| | |
|---|---|
| *A61B 18/18* | (2006.01) |
| *A61B 18/14* | (2006.01) |
| *A61B 17/29* | (2006.01) |
| *A61B 18/00* | (2006.01) |

(52) U.S. Cl.
CPC .......... *A61B 18/1445* (2013.01); *A61B 17/29* (2013.01); *A61B 2017/2924* (2013.01); *A61B 2017/2936* (2013.01); *A61B 2017/2939* (2013.01); *A61B 2018/00339* (2013.01); *A61B 2018/00577* (2013.01); *A61B 2018/00607* (2013.01); *A61B 2018/1407* (2013.01); *A61B 2218/007* (2013.01)

(58) Field of Classification Search
CPC ...... A61B 18/1445; A61B 2018/00339; A61B 2018/00577; A61B 2018/00607; A61B 2018/1407; A61B 2218/007; A61B 17/221; A61B 17/29; A61B 2017/2901; A61B 2017/2902; A61B 2017/2905; A61B 2017/2908; A61B 17/2909; A61B 2017/291; A61B 2017/2912; A61B 2017/2916; A61B 2017/2919; A61B 2017/292; A61B 2017/2922; A61B 2017/2924; A61B 2017/2925
See application file for complete search history.

(56) References Cited

U.S. PATENT DOCUMENTS

| | | | | |
|---|---|---|---|---|
| 4,353,371 | A | * 10/1982 | Cosman | A61B 17/30 606/42 |
| 4,832,683 | A | 5/1989 | Idemoto et al. | |
| 5,085,657 | A | 2/1992 | Ben-Simhon | |
| 5,190,541 | A | * 3/1993 | Abele | A61B 18/1442 604/35 |
| 5,197,964 | A | * 3/1993 | Parins | A61B 18/1442 606/48 |
| 5,484,441 | A | * 1/1996 | Koros | A61B 17/1611 606/79 |
| 5,849,028 | A | 12/1998 | Chen | |

(Continued)

FOREIGN PATENT DOCUMENTS

| | | |
|---|---|---|
| EP | 1026996 B1 | 8/2000 |
| EP | 1061857 B1 | 12/2000 |

*Primary Examiner* — Michael Peffley
*Assistant Examiner* — Amanda Zink

(57) ABSTRACT

An electro-surgical instrument includes a first member extending to an end having a first electrode. A second member extends to an end having a second return electrode. The ends define a spinal tissue cavity and are relatively translatable to selectively adjust the cavity such that the electrodes are oriented to ablate, cut and/or coagulate spinal tissue. Systems and methods are disclosed.

20 Claims, 5 Drawing Sheets

(56) References Cited

U.S. PATENT DOCUMENTS

| | | | |
|---|---|---|---|
| 6,267,761 B1 * | 7/2001 | Ryan | A61B 18/1442 606/32 |
| 6,348,051 B1 | 2/2002 | Farin et al. | |
| 6,379,350 B1 | 4/2002 | Sharkey et al. | |
| 6,558,385 B1 * | 5/2003 | McClurken | A61B 18/1442 606/46 |
| 6,802,842 B2 | 10/2004 | Ellman et al. | |
| 6,905,498 B2 * | 6/2005 | Hooven | A61B 18/1445 606/50 |
| 7,303,559 B2 | 12/2007 | Peng et al. | |
| 7,347,857 B2 | 3/2008 | Anderson et al. | |
| 8,177,783 B2 | 5/2012 | Davison et al. | |
| 8,262,655 B2 | 9/2012 | Ghabrial et al. | |
| 8,308,722 B2 | 11/2012 | Ormsby et al. | |
| 9,072,522 B2 * | 7/2015 | Morejohn | A61B 18/1442 |
| 2003/0181904 A1 | 9/2003 | Levine et al. | |
| 2004/0162553 A1 | 8/2004 | Peng et al. | |
| 2006/0084974 A1 * | 4/2006 | Privitera | A61B 18/1445 606/50 |
| 2006/0085021 A1 * | 4/2006 | Wenzler | A61B 17/1611 606/184 |
| 2006/0100619 A1 * | 5/2006 | McClurken | A61B 18/1442 606/45 |
| 2010/0023007 A1 | 1/2010 | Sartor et al. | |
| 2013/0338658 A1 * | 12/2013 | Zada | A61B 18/08 606/29 |
| 2014/0257301 A1 * | 9/2014 | Greeley | A61B 17/1606 606/83 |
| 2015/0038964 A1 * | 2/2015 | Dickson | A61B 18/085 606/45 |
| 2015/0209060 A1 * | 7/2015 | Dmuschewsky | A61B 17/1608 606/207 |

\* cited by examiner

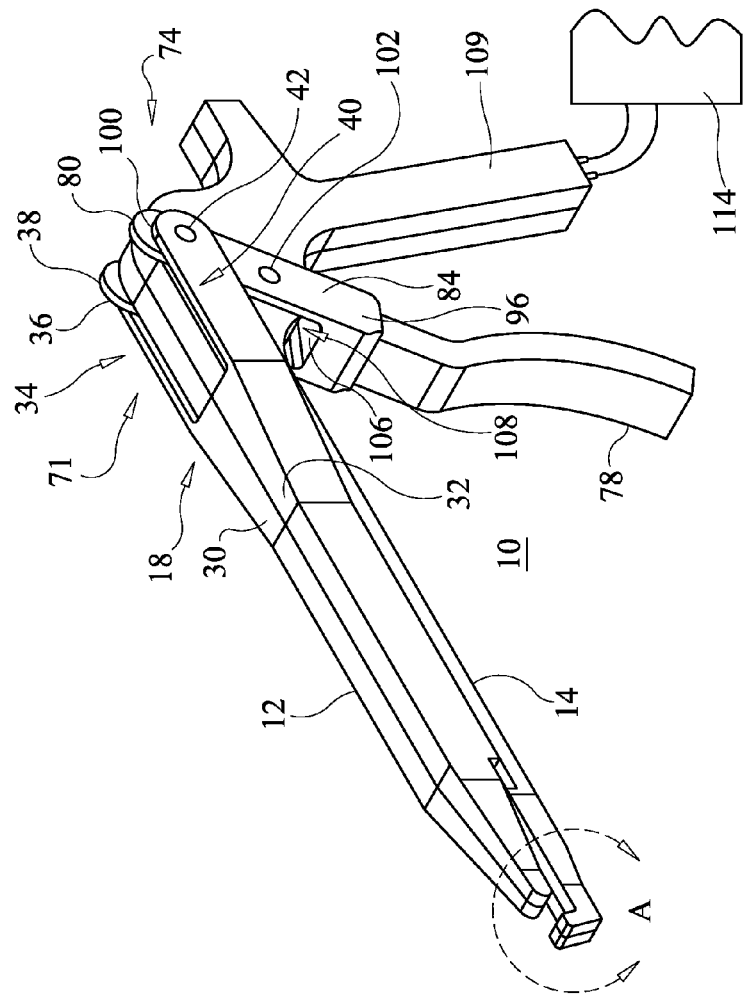
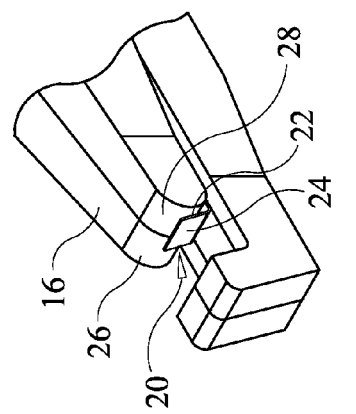
FIG. 2
FIG. 3

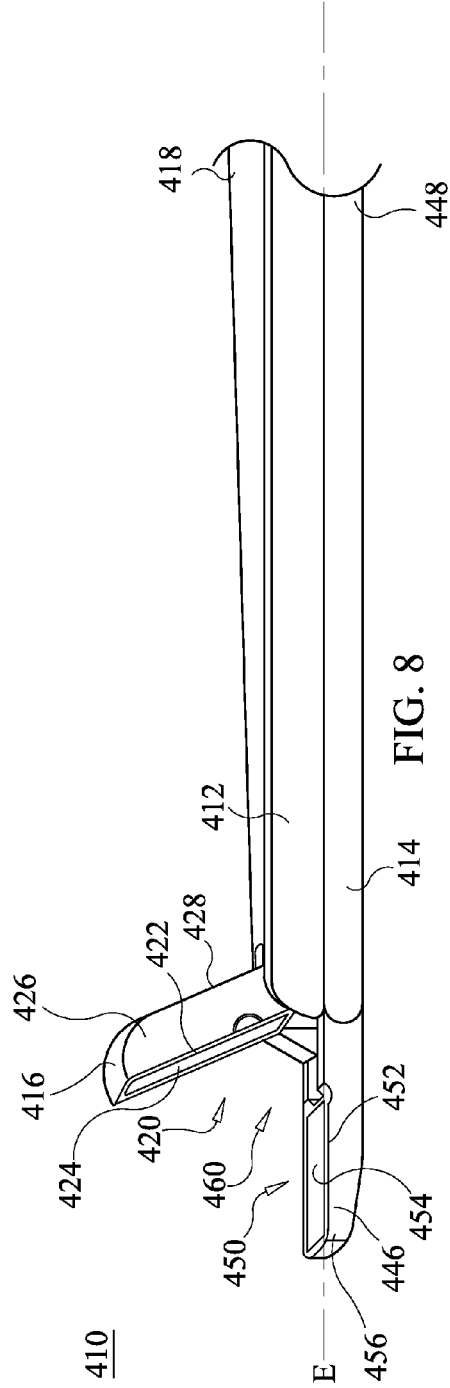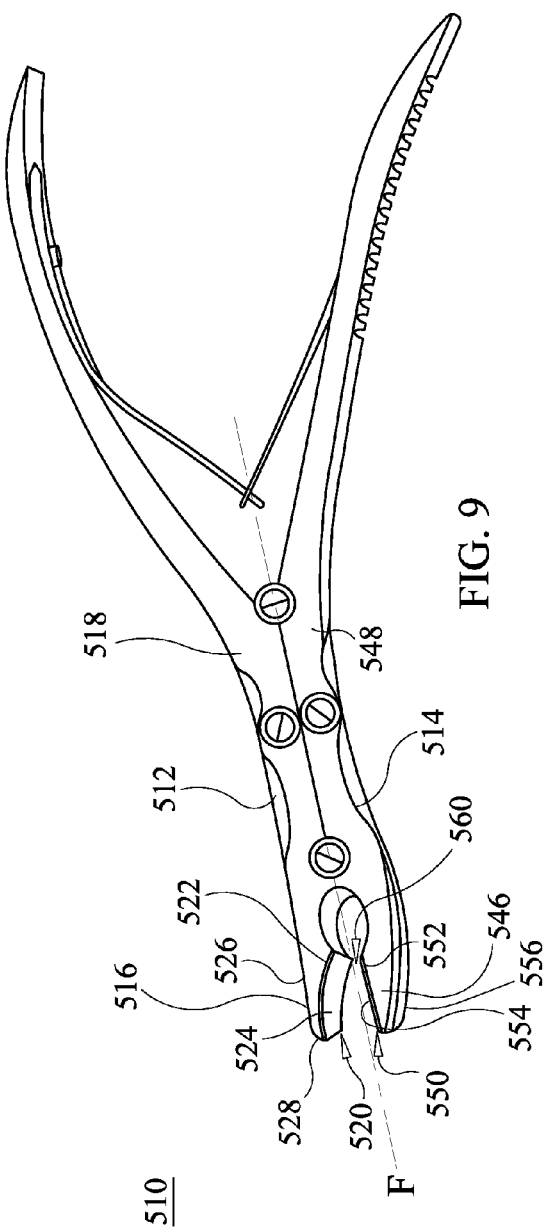

SURGICAL INSTRUMENT AND METHOD

TECHNICAL FIELD

The present disclosure generally relates to medical devices for the treatment of musculoskeletal disorders, and more particularly to a spinal surgery system for treating pathologies of the spine and a method for treating a spine.

BACKGROUND

Spinal pathologies and disorders such as degenerative disc disease, disc herniation, osteoporosis, scoliosis and other curvature abnormalities, kyphosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, decompression, laminectomy, fusion and implantable prosthetics. As part of these surgical treatments, spinal constructs, such as, for example, bone fasteners, spinal rods and interbody devices can be used to provide stability to a treated region. For example, during surgical treatment, surgical instruments can be used to cut, resect and/or remove spinal tissue. This disclosure describes an improvement over these prior art technologies.

SUMMARY

In one embodiment, an electro-surgical instrument is provided. The electro-surgical instrument includes a first member extending to an end having a first electrode. A second member extends to an end having a second return electrode. The ends define a spinal tissue cavity and are relatively translatable to selectively adjust the cavity such that the electrodes are oriented to ablate, cut and/or coagulate spinal tissue. In some embodiments, systems and methods are provided.

BRIEF DESCRIPTION OF THE DRAWINGS

The present disclosure will become more readily apparent from the specific description accompanied by the following drawings, in which:

FIG. 2 is a perspective view of the components shown in FIG. 1;

FIG. 3 is a perspective view of the components shown in detail A in FIG. 2;

FIG. 8 is a break away perspective view of components of one embodiment of a system in accordance with the principles of the present disclosure; and FIG. 9 is a perspective view of components of one embodiment of a system in accordance with the principles of the present disclosure.

DETAILED DESCRIPTION

Figure 1:
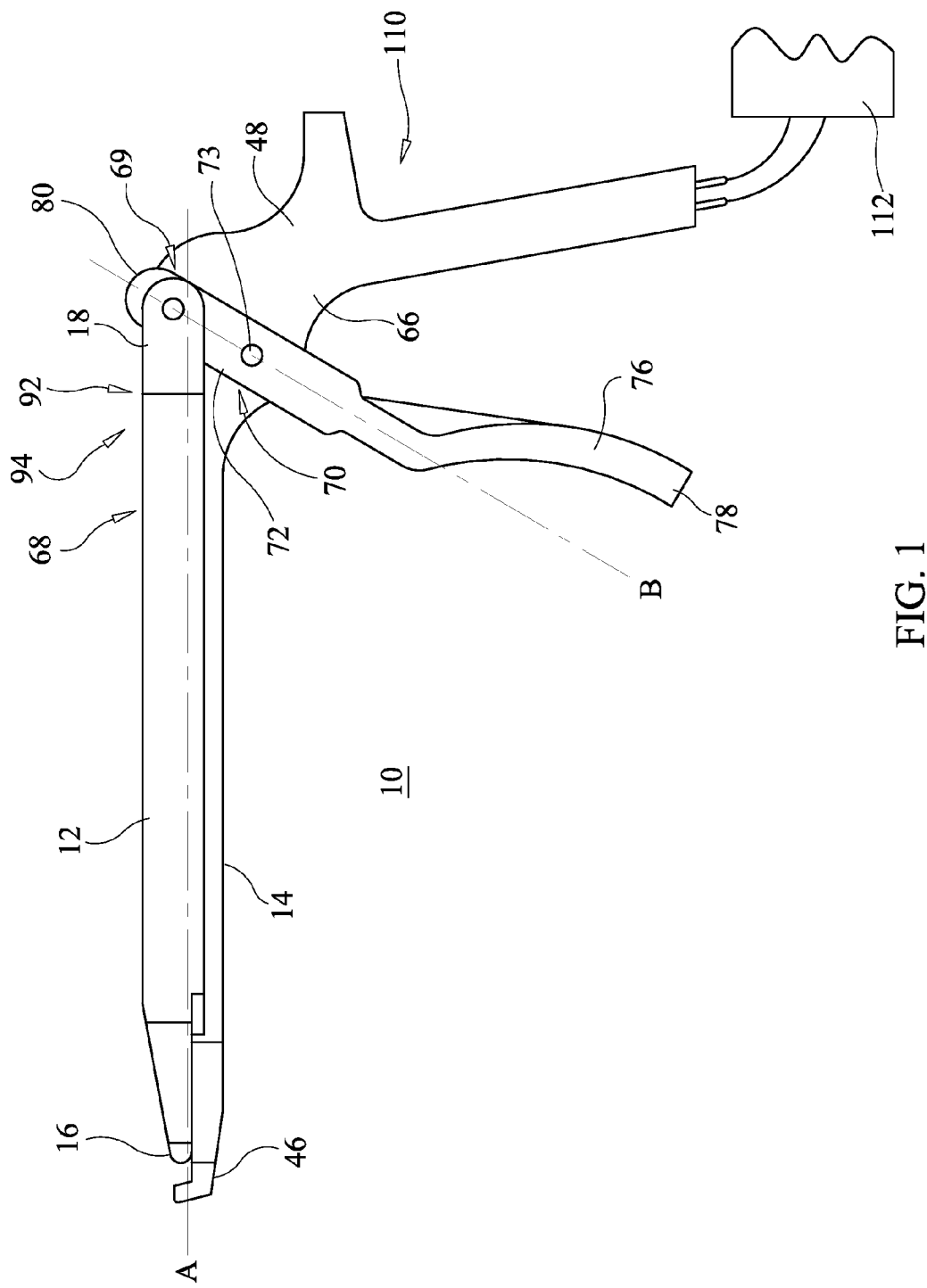
FIG. 1 is a side view of components of one embodiment of a system in accordance with the principles of the present disclosure.
Figure 4:
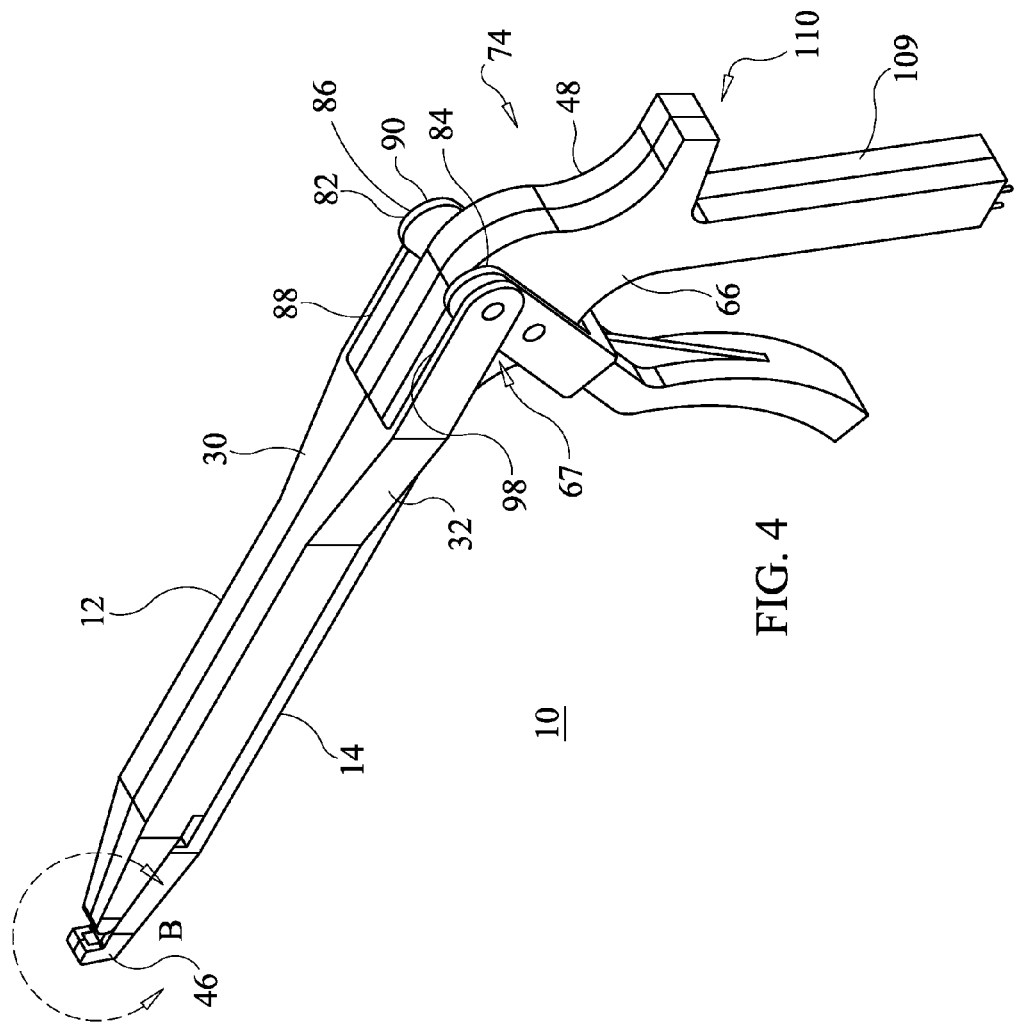
FIG. 4 is a perspective view of the components shown in FIG. 1.
Figure 5:
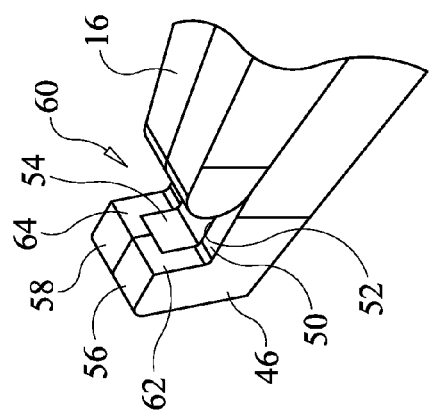
FIG. 5 is a perspective view of the components shown in detail B in FIG. 4.

The exemplary embodiments of the system and related methods of use disclosed are discussed in terms of surgical instruments for the treatment of musculoskeletal disorders and more particularly, in terms of a surgical system and method for treatment of a spine disorder.

In one embodiment, the present surgical system includes a radiofrequency (RF) ablation instrument. In some embodiments, the instrument is configured for RF ablation, electrosurgical, plasma coagulation and/or cutting. In one embodiment, the RF ablation instrument can be employed for resisting and/or preventing excessive bleeding during a posterior longitudinal ligament resection (PLL) of spinal tissue. In one embodiment, the RF ablation instrument can be employed for resisting and/or preventing excessive bleeding during a PLL during an anterior cervical discectomy and fusion (ACDF), for example, used for decompression of vertebrae. In one embodiment, the RF ablation instrument can be employed for resisting and/or preventing excessive bleeding of a ligamentum flavum and associated vasculature during a posterior lumbar fusion.

In some embodiments, the RF ablation, electrosurgical, plasma coagulation and/or cutting instrument includes ends that cut vertebral tissue and coagulate vertebral tissue. For example, as the ends are cutting, electrodes disposed with the ends cauterize and/or ablate the cut tissue to stop the bleeding. In some embodiments, the RF ablation instrument includes a rongeur instrument, such as, for example, a Kerrison configuration, which is provided to stop excessive venous bleeding during PLL resection and in ACDF or cervical arthroplasty, or other spinal procedures where bleeding is encountered while using a rongeur. In some embodiments, a RF ablation instrument is provided to stop excessive venous bleeding during posterior lumbar fusion, in the ligamentum flavum and associated excessive vascular bleeding.

In one embodiment, the RF ablation, electrosurgical, plasma coagulation and/or cutting instrument includes disc removal curettes used for mechanical disc cutting and removal with an ablative RF component. In some embodiments, the RF ablation instrument comprises one or a plurality of disc removal curettes. In some embodiments, the disc removal curette comprises an insulated inner surface configured to protect end plates of the instrument. In some embodiments, the RF ablation instrument includes a loop portion that includes an insulated inner surface configured to protect end plates.

In some embodiments, the RF ablation, electrosurgical, plasma coagulation and/or cutting instrument is disposable and bipolar. In some embodiments, the RF ablation instrument comprises a bipolar electrocautery configuration.

The present disclosure may be understood more readily by reference to the following detailed description of the disclosure taken in connection with the accompanying drawing figures, which form a part of this disclosure. It is to be understood that this disclosure is not limited to the specific instruments, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, vessels, ligaments, tendons, cartilage and/or bone unless specifically referred to otherwise.

The following discussion includes a description of a surgical system including surgical instruments, related components and methods of employing the system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, RF ablation instrument 10 in accordance with the principles of the present disclosure.

The components of RF ablation, electrosurgical, plasma coagulation and/or cutting instrument 10 can be fabricated from biologically acceptable materials suitable for medical applications, including metals, synthetic polymers, and/or their composites. For example, the components of RF ablation instrument 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations, biocompatible ceramics, or any combination thereof.

Various components of RF ablation, electrosurgical, plasma coagulation and/or cutting instrument 10 may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of RF ablation instrument 10 may be monolithically formed, integrally connected or include fastening elements and/or instruments, as described herein.

RF ablation, electrosurgical, plasma coagulation and/or cutting instrument 10 is employed, for example, with a minimally invasive procedure, including percutaneous techniques, and mini-open surgical techniques to cut, ablate, resect and/or remove spinal tissue, for surgical treatment at a surgical site within a body of a patient, for example, a section of a spine to treat various spine pathologies, such as, for example, those described herein. In some embodiments, the surgical system may comprise various instruments, such as, for example, inserters, extenders, reducers, spreaders, distractors, blades, clamps, forceps, elevators and drills, which may be alternately sized and dimensioned, and arranged as a kit.

RF ablation, electrosurgical, plasma coagulation and/or cutting instrument 10 includes a member 12 and a member 14. Member 12 defines a longitudinal axis A, and member 12 translates relative to member 14 along axis A. Member 12 extends between a distal end 16 and a proximal end 18. Member 12 includes an inner surface 20 that extends between ends 16 and 18.

Surface 20 defines a channel 22 configured for disposal of a first electrode 24 disposed adjacent end 16 and electrically communicating with end 18. End 16 includes an insulator 26 configured for disposal between electrode 24 and adjacent tissue disposed at a surgical site. End 16 includes an outer layer 28 configured to electrically insulate electrode 24 from adjacent tissue. In some embodiments, insulator 26 and layer 28 can be glass or ceramic having a thickness from about 0.005 to about 0.5 mm thick or from about 0.01 to about 0.2 mm thick. In various embodiments, end 16 comprises a curette configuration. In some embodiments, end 16 comprises a ronguer configuration.

End 18 includes an arm 30 and an arm 32. Arms 30, 32 are disposed in a parallel configuration. In some embodiments, all or only a portion of arms 30, 32 may be disposed in alternate orientations, relative to axis A, such as, for example, transverse, perpendicular and/or other angular orientations such as acute or obtuse, co-axial and/or may be offset or staggered. Arms 30, 32 are configured for engagement with an end of member 14 and an actuator, as described herein.

Arm 30 includes a surface 34 that defines an opening 36. Opening 36 is configured for disposal of a pivoting member such as, for example, a pin 38. Arm 32 includes a surface 40 that defines an opening 42. Opening 42 is configured for disposal of pin 38. In some embodiments, alternative pivoting members include a rod, screw or clip may be employed.

Member 14 extends between a distal end 46 and a proximal end 48. Member 14 includes an inner surface 50 extending between ends 46, 48. Surface 50 defines a channel 52 configured for disposal of a return electrode 54 at end 46. In some embodiments, electrodes 24, 54 are disposed in a bipolar configuration. End 46 includes an insulator 56 configured for disposal between electrode 54 and an adjacent tissue at a surgical site. In some embodiments, insulator 56 can be glass or ceramic having a thickness from about 0.005 to about 0.5 mm thick or from about 0.01 to about 0.2 mm thick. End 46 includes a blunt tip 58 configured to resist and/or prevent undesired engagement and/or damage to adjacent tissue at a surgical site. In some embodiments, tip 58 is rounded and/or somewhat pointed to allow for easy penetration through tissue. In various embodiments, end 46 comprises a curette configuration. In some embodiments, end 46 comprises a ronguer configuration.

End 16 of member 12 and end 46 of member 14 define a tissue cavity 60 for targeting and/or capturing selected spinal tissue. Ends 16, 46 are relatively translatable to target and/or cut, resect and/or remove selected tissue at a surgical site. Ends 16, 46 are relatively translatable to selectively adjust cavity 60 for capture of selected tissue at a surgical site such that electrodes 24, 54 are oriented to ablate tissue, such as, for example, intervertebral tissue. Cavity 60 includes an inner surface 62 that defines an inner edge 64. Edge 64 is configured to cut and capture tissue. Cavity 60 is configured to receive tissue as edge 64 separates tissue. In some embodiments, end 16 and/or end 46 can comprise a scalpel, one or more cutting blades, scissors, forceps, a probe, a bipolar electrode, a unipolar electrode, a thermal electrode and/or a needle.

In some embodiments, cavity 60 is an intervertebral tissue cavity. In some embodiments, cavity 60 is a ligament tissue cavity. Cavity 60 can be configured to allow for nerve and/or soft tissue to be pulled back into cavity 60 and ablated or resected with pulsed plasma and/or radio frequency discharges. In some embodiments, cavity 60 is scoop shaped. In various embodiments, cavity 60 is shaped as a regular or irregular polygon including arcuate, c-shaped, round, square, oblong, kidney shaped, crescent, or beveled shape with or without ridges. In one embodiment, members 12, 14 form a hollowed-out conduit such that cavity 60 receives and emits pulsed plasma or RF discharges adapted for cutting nerve and/or soft tissue from a plasma generator or RF generator, as described herein.

End 48 comprises an outer surface 66 that defines an aperture, such as, for example, a slot 67. Slot 67 includes a distal portion 68 and a proximal portion 69. Slot 67 is configured for disposal of pin 38 such that pin 38 translates along axis A to facilitate movement of member 12 relative to member 14.

Surface 66 defines a passageway 70. Passageway 70 includes an opening 71 and an opening 72 configured for disposal of a pin 73. Pin 73 is configured to facilitate rotation of a lever, as described herein, to facilitate movement of pin 38 within slot 67 such that member 12 translates relative to member 14 for targeting, capture, cutting and/or ablating tissue, as described herein. In some embodiments, at least a portion of end 48 is angular and is configured for engagement with end 18 of member 12 and an actuator, as described herein.

RF ablation, electrosurgical, plasma coagulation and/or cutting instrument 10 includes an actuator 74. Actuator 74 is connected to members 12, 14 at ends 18, 48 respectively, and is configured to translate ends 16, 46 to selectively adjust cavity 60, such that electrodes 24, 54 are oriented to ablate tissue. In one embodiment, actuator 74 includes a first portion, such as, for example, a lever 76. Lever 76 extends between a portion 78 and a portion 80. Lever 76 defines a longitudinal axis B. In some embodiments, at least a part of portion 78 is angled. In some embodiments, portion 78 is linear.

Portion 80 includes an extension 82 and an extension 84. Extension 82 comprises an outer surface 86. Surface 86 is configured for engagement with an inner surface 88 of arm 30. Surface 86 defines a recess 90 configured for engagement with pin 38. Surface 86 defines a recess 92 configured for engagement with pin 73. Extension 84 comprises an outer surface 96. Surface 96 is configured for engagement with an inner surface 98 of arm 32. Surface 96 defines a recess 100 configured for engagement with pin 38. Surface 96 defines a recess 102 configured for engagement with pin 73.

An inner surface 106 of lever 76 defines a cavity 108 disposed between extensions 82, 84. Cavity 108 is configured for disposal of end 48 of member 14. In some embodiments, cavity 108 is U-shaped. In some embodiments, all or only a portion of cavity 108 may have alternate cross section configurations, such as, for example, oval, oblong, triangular, square, polygonal, irregular, uniform, non-uniform, offset, staggered, undulating, arcuate, variable and/or tapered.

Actuator 74 comprises an arm 109 having a pistol grip configuration 110. In one embodiment, actuator 74 includes a Kerrison type grip or a scissor type grip. In one embodiment, members 12, 14 and/or lever 76 are detachable such that members 12, 14 and/or lever 76 are disposable and/or removable for cleaning. In one embodiment, members 12, 14 and/or lever 76 are partially or entirely plastic such that the entire instrument could be disposable.

In some embodiments, RF ablation instrument 10 comprises an RF generator 112 configured for supplying electric current to electrodes 24, 54. In some embodiments, RF ablation instrument 10 comprises a vacuum source 114 configured to communicate with ends 16, 46. In one embodiment, RF ablation instrument 10 includes an internal passage (not shown) configured to engage vacuum source 114, to remove ablated, cut and/or resected tissue via suction. The passage may extend partially through member 12 and/or or may extend through member 14 to edge 64. Alternatively, an additional channel is possible for delivering fluid to the surgical site. At end 48, member 14 can be operatively connected to vacuum source 114 for providing suction to ablated cut and/or resected tissue. In some embodiments, any suitable aspirator, cylindrical or otherwise, or other mechanism that creates vacuum upon the movement of an actuating member thereof, may be utilized as a vacuum source, such as, for example, a syringe or a mechanical vacuum. In one embodiment, vacuum source 114 is in communication with cavity 60 for providing suction to remove cut nerve and/or soft tissue.

In one embodiment, RF ablation instrument 10 is operatively connected to semi-steerable or navigational sources for easier guidance into tissues. In one embodiment, the navigational source is coupled with a pre-procedure imaging means such as for example, CT, MRI, PET scan, etc. so that the target intervertebral, ligament, nerve or other soft tissue to be cut can be identified and accurately located during the procedure.

In some embodiments, electrodes 24, 54 can be adapted to receive an RF waveform from an RF generator. In some embodiments, the RF generator may be a conventional, bipolar/monopolar electrosurgical having predetermined frequency, amplitude, and pulse width suitable to destroy tissues in the form of direct current electrical pulses delivered at a frequency in the range of 1-20 Hz, amplitude in the range of 100-1000 VDC, and pulse width in the range of 0.01-100 ms. In some embodiments, the RF generator may be a conventional, bipolar/monopolar electrosurgical generator.

In assembly, operation and use, the surgical system, similar to the systems described herein, includes RF ablation instrument 10, which is employed with a surgical procedure, such as, for example, a PLL during an ACDF for treatment of a spine (not shown) of a patient including vertebrae and intervertebral tissue. RF ablation instrument 10 may also be employed with other surgical procedures, such as, for example, discectomy, laminectomy, lumbar fusion, laminotomy, laminectomy, nerve root retraction, foramenotomy, facetectomy, decompression, spinal nucleus or disc replacement and bone graft and implantable prosthetics including interbody devices, plates, rods, and bone engaging fasteners.

RF ablation instrument 10 is employed with an ACDF to immobilize a cervical joint for treatment of an applicable condition or injury of an affected section of a spinal column and adjacent areas within a body. In use, to treat the affected section of vertebrae, a medical practitioner obtains access to a surgical site including the vertebrae in any appropriate manner, such as through incision and retraction of tissues. In some embodiments, RF ablation instrument 10 may be used in any existing surgical method or technique including open surgery, mini-open surgery, minimally invasive surgery and percutaneous surgical implantation, whereby vertebrae are accessed through a mini-incision, or sleeve that provides a protected passageway to the area.

Once access to the surgical site is obtained, RF ablation instrument 10 is manipulated to dispose ends 16, 46 adjacent the surgical site including the posterior longitudinal ligament. Tissue of the posterior longitudinal ligament is targeted with tissue cavity 60. Ends 16, 46 are relatively translatable to selectively adjust such that tissue of the posterior longitudinal ligament is captured within tissue cavity 60. Ends 16, 46 cut, resect and/or remove tissue of the posterior longitudinal ligament at the surgical site. Ends 16, 46 are relatively translatable such that electrodes 24, 54 are oriented to apply RF energy to the tissue and ablate the tissue of and/or adjacent to the posterior longitudinal ligament to resist and/or prevent excessive bleeding of the tissue. In some embodiments, such tissue includes intervertebral tissue and other soft and nerve tissues, to resist and/or prevent excessive bleeding of the tissue.

Upon completion of a procedure, as described herein, the surgical instruments, assemblies and non-implanted components of the surgical system are removed and the incision(s) are closed. One or more of the components of the surgical system can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of the surgical system.

Figure 6:
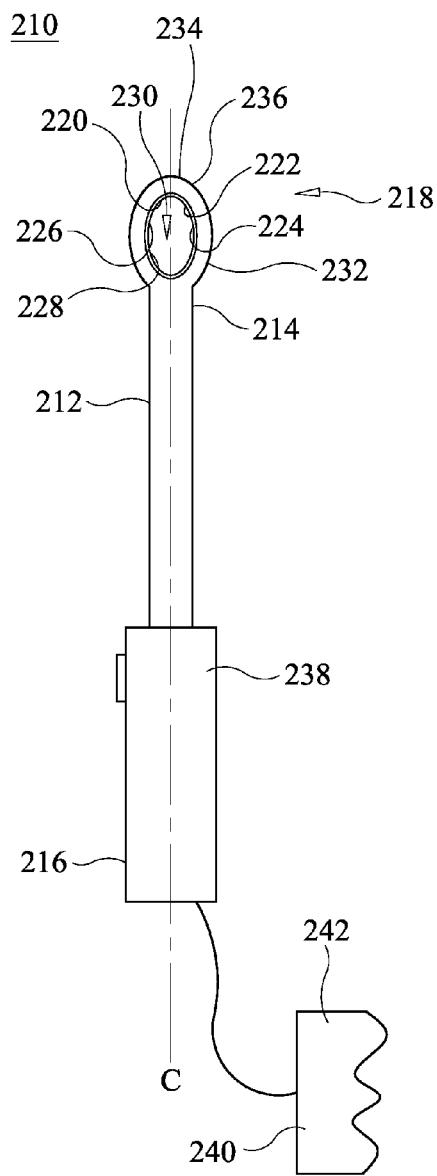
FIG. 6 is a side view of components of one embodiment of a system in accordance with the principles of the present disclosure.

In one embodiment, as shown in FIG. 6, the surgical system, similar to the systems and methods described herein, comprises an RF ablation instrument 210, similar to RF ablation instrument 10 described above with regard to FIGS. 1-5, which includes a member, such as, for example, an arm 212 extending between a distal end 214 and a proximal end 216. A longitudinal axis C extends between ends 214, 216. End 214 defines a loop 218 configuration. In some embodiments, loop 218 is a closed loop. Loop 218 includes an inner surface 220. Surface 220 defines a portion 222 having an electrode 224. Surface 220 defines a portion 226 having a return electrode 228.

In various embodiments, portion 226 faces portion 222. In some embodiments, portions 222, 226 define an intervertebral tissue cavity 230 configured and oriented to ablate intervertebral tissue. Loop 218 includes an outer surface 232 that defines a blunt surface 234 configured to protect adjacent tissue. In some embodiments, arm 212 includes an outer layer 236 disposed at end 214 configured to electrically insulate loop 218 from adjacent tissue. In some embodiments, layer 236 can be glass or ceramic.

End 216 comprises a handle 238. In some embodiments, an RF generator 240 for supplying electric current to electrodes 224, 228 is configured for engagement with RF ablation instrument 210. In various embodiments, RF generator 240 is disposed at end 216. In some embodiments, RF ablation instrument 210 includes a vacuum source 242 configured to communicate with end 216. In one embodiment, RF ablation instrument 210 includes an internal passage (not shown) configured to engage vacuum source 242, to remove ablated and/or resected tissue via suction. The passage may extend partially through arm 212. Alternatively, an additional channel is possible for delivering fluid to the surgical site. At end 216, arm 212 can be operatively connected to vacuum source 242 for providing suction to ablated and/or resected tissue. In one embodiment, vacuum source 242 is in communication with cavity 230 for providing suction to remove cut nerve and/or soft tissue.

Figure 7:
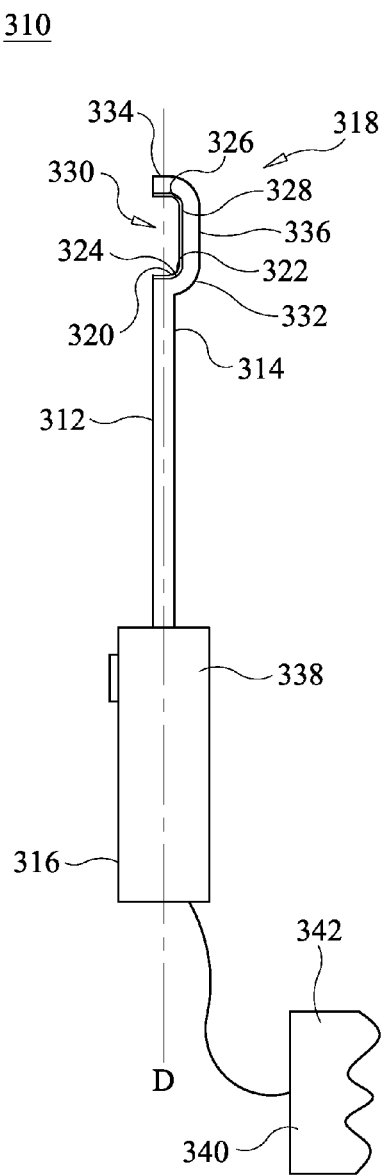
FIG. 7 is a side view of components of one embodiment of a system in accordance with the principles of the present disclosure.

In one embodiment, as shown in FIG. 7, the surgical system, similar to the systems and methods described herein, comprises an RF ablation instrument 310, similar to RF ablation instrument 210 described above, which includes a member, such as, for example, an arm 312 extending between a distal end 314 and a proximal end 316. A longitudinal axis D extends between ends 314 and 316. End 314 defines a curette 318. Curette 318 includes an inner surface 320. Surface 320 defines a portion 322 having an electrode 324. Surface 320 defines a portion 326 having a return electrode 328. In some embodiments, portions 322, 326 define an intervertebral tissue recess 330 configured and oriented to ablate intervertebral tissue. Curette 318 includes an outer surface 332 that defines a blunt surface 334 configured to protect adjacent tissue. In some embodiments, arm 312 includes an outer layer 336 disposed at end 314 configured to electrically insulate curette 318 from adjacent tissue. In some embodiments, layer 336 can be glass or ceramic.

End 316 comprises a handle 338. In some embodiments, an RF generator 340 for supplying electric current to electrodes 324, 328 is configured for engagement with RF ablation instrument 310. In various embodiments, RF generator 340 is disposed at end 316. In some embodiments, RF ablation instrument 310 includes a vacuum source 342 configured to communicate with end 316. In one embodiment, RF ablation instrument 310 includes an internal passage (not shown) configured to engage vacuum source 342, to remove ablated and/or resected tissue via suction. The passage may extend partially through arm 312. Alternatively, an additional channel is possible for delivering fluid to the surgical site. At end 316, arm 312 can be operatively connected to vacuum source 342 for providing suction to ablated and/or resected tissue. In one embodiment, vacuum source 342 is in communication with recess 330 for providing suction to remove cut nerve and/or soft tissue.

In one embodiment, as shown in FIG. 8, the surgical system, similar to the systems and methods described herein, comprises an RF ablation instrument 410, similar to RF ablation instrument 10 described above with regard to FIGS. 1-5. In one embodiment, RF ablation instrument 410 is a bipolar pituitary rongeur. RF ablation Instrument 410 includes a member 412 and a member 414, similar to members 12, 14 as described above. Members 412, 414 define a longitudinal axis E. Member 412 includes a distal end 416 and a proximal end 418. Member 412 includes an inner surface 420 that extends between ends 416, 418.

Surface 420 defines a channel 422 configured for disposal of a first electrode 424 disposed adjacent end 416 and electrically communicating with end 418. End 416 includes an insulator 426 configured for disposal between electrode 424 and adjacent tissue disposed at a surgical site. End 416 includes an outer layer 428 configured to electrically insulate electrode 424 from adjacent tissue. In some embodiments, insulator 426 and layer 428 can be glass or ceramic having a thickness from about 0.005 to about 0.5 mm thick or from about 0.01 to about 0.2 mm thick.

Member 414 extends between a distal end 446 and a proximal end 448. Member 414 includes an inner surface 450 extending between ends 446, 448. Surface 450 defines a channel 452 configured for disposal of a return electrode 454 at end 446. In some embodiments, electrodes 424, 454 are disposed in a bipolar configuration. End 446 includes an insulator 456 configured for disposal between electrode 454 and an adjacent tissue at a surgical site. In some embodiments, insulator 456 can be glass or ceramic having a thickness from about 0.005 to about 0.5 mm thick or from about 0.01 to about 0.2 mm thick.

End 416 of member 412 and end 446 of member 414 define a tissue cavity 460 for targeting and/or capturing selected spinal tissue. Ends 416, 446 are relatively translatable to target and/or cut, resect and/or remove selected tissue at a surgical site. Ends 416, 446 are rotatable to selectively adjust cavity 460 for capture of selected tissue at a surgical site such that electrodes 424, 454 are oriented to ablate tissue, such as, for example, intervertebral tissue. In some embodiments, end 416 and/or end 446 can comprise a scalpel, one or more cutting blades, scissors, forceps, a probe, a bipolar electrode, a unipolar electrode, a thermal electrode and/or a needle.

In some embodiments, cavity 460 is an intervertebral tissue cavity. In some embodiments, cavity 460 is a ligament tissue cavity. Cavity 460 can be configured to allow for nerve and/or soft tissue to be pulled back into cavity 460 and ablated or resected with pulsed plasma and/or radio frequency discharges. In some embodiments, cavity 460 is v-shaped. In various embodiments, cavity 460 is shaped as a regular or irregular polygon including scoop shaped, arcuate, c-shaped, round, square, oblong, kidney shaped, crescent, or beveled shape with or without ridges. In one embodiment, members 412, 414 form a hollowed-out conduit such that cavity 460 receives and emits pulsed plasma or RF discharges adapted for cutting nerve and/or soft tissue from a plasma generator or RF generator, as described herein.

In one embodiment, as shown in FIG. 9, the surgical system, similar to the systems and methods described herein, comprises an RF ablation instrument 510, similar to RF ablation instrument 10 described above with regard to FIGS. 1-5. In one embodiment, RF ablation instrument 510 is a leksell rongeur. RF ablation Instrument 510 includes a member 512 and a member 514, similar to members 12, 14 as described above. Members 512, 514 are pivotable relative to each other and define a longitudinal axis F. Member 512 includes a distal end 516 and a proximal end 518. Member 512 includes an inner surface 520 that extends between ends 516, 518.

Surface 520 defines a channel 522 configured for disposal of a first electrode 524 disposed adjacent end 516 and electrically communicating with end 518. End 516 includes an insulator 526 configured for disposal between electrode 524 and adjacent tissue disposed at a surgical site. End 516 includes an outer layer 528 configured to electrically insulate electrode 524 from adjacent tissue. In some embodiments, insulator 526 and layer 528 can be glass or ceramic having a thickness from about 0.005 to about 0.5 mm thick or from about 0.01 to about 0.2 mm thick.

Member 514 extends between a distal end 546 and a proximal end 548. Member 514 includes an inner surface 550 extending between ends 546, 548. Surface 550 defines a channel 552 configured for disposal of a return electrode 554 at end 546. In some embodiments, electrodes 524, 554 are disposed in a bipolar configuration. End 546 includes an insulator 556 configured for disposal between electrode 554 and an adjacent tissue at a surgical site. In some embodiments, insulator 556 can be glass or ceramic having a thickness from about 0.005 to about 0.5 mm thick or from about 0.01 to about 0.2 mm thick.

End 516 of member 512 and end 546 of member 514 define a tissue cavity 560 for targeting and/or capturing selected spinal tissue. Ends 516, 546 are relatively pivotable to target and/or cut, resect and/or remove selected tissue at a surgical site. Ends 516, 546 are pivotable to selectively adjust cavity 560 for capture of selected tissue at a surgical site such that electrodes 524, 554 are oriented to ablate tissue, such as, for example, intervertebral tissue. In some embodiments, end 516 and/or end 546 can comprise a scalpel, one or more cutting blades, scissors, forceps, a probe, a bipolar electrode, a unipolar electrode, a thermal electrode and/or a needle.

In some embodiments, cavity 560 is an intervertebral tissue cavity. In some embodiments, cavity 560 is a ligament tissue cavity. Cavity 560 can be configured to allow for nerve and/or soft tissue to be pulled back into cavity 560 and ablated or resected with pulsed plasma and/or radio frequency discharges. In some embodiments, cavity 560 is c-shaped. In various embodiments, cavity 560 is shaped as a regular or irregular polygon including scoop shaped, arcuate, v-shaped, round, square, oblong, kidney shaped, crescent, or beveled shape with or without ridges. In one embodiment, members 512, 514 form a hollowed-out conduit such that cavity 560 receives and emits pulsed plasma or RF discharges adapted for cutting nerve and/or soft tissue from a plasma generator or RF generator, as described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An electro-surgical instrument comprising:
   a first member extending between a first end having a first electrode and a second end having spaced apart arms;
   a second member extending along a longitudinal axis between a first end having a second return electrode and a second end having a slot, the first ends defining a tissue cavity;
   a lever comprising spaced apart extensions, outer surfaces of the extensions engaging inner surfaces of the arms and an outer surface of the second end of the second member engaging inner surfaces of the extensions;
   a first pin extending through the arms, the extensions and the slot; and
   a second pin extending through the extensions and the second end of the second member, wherein pivoting the lever relative to the second member about the second pin translates the first in within the slot to move the first member relative to the second member along the longitudinal axis to selectively adjust a length of the cavity.

2. An electro-surgical instrument as recited in claim 1, wherein the electro-surgical instrument comprises an actuator comprising the lever and handle arm, the actuator having a pistol grip configuration.

3. An electro-surgical instrument as recited in claim 1, further comprising an RF generator for supplying electric current to the electrodes.

4. An electro-surgical instrument as recited in claim 1, wherein the electrodes are disposed in a bipolar configuration.

5. An electro-surgical instrument as recited in claim 1, wherein the first ends each include an insulator configured for disposal between the electrodes and the adjacent tissue.

6. An electro-surgical instrument as recited in claim 1, wherein the first end of the second member includes a blunt tip configured to protect adjacent tissue.

7. An electro-surgical instrument as recited in claim 1, further comprising a vacuum source communicating with the first ends.

8. An electro-surgical instrument as recited in claim 1, wherein the first end of the first member includes an outer layer disposed to electrically insulate the first electrode from adjacent tissue.

9. An electro-surgical instrument as recited in claim 1, wherein the first ends comprise a curette.

10. An electro-surgical instrument as recited in claim 1, wherein the first ends comprise a rongeur configuration.

11. An electro-surgical instrument as recited in claim 1, wherein the second pin is spaced apart from the first member.

12. An electro-surgical instrument as recited in claim 1, wherein the lever is movable relative to the second member between a first position in which the cavity has a first length and a second position in which the cavity has an increased second length, the lever not being biased to the first position or the second position.

13. An electro-surgical instrument as recited in claim 1, wherein the slot includes a first end and an opposite second end, the cavity having a first length when the first pin is positioned at the first end of the slot and an increased second length when the first pin is positioned at the second end of the slot.

14. An electro-surgical instrument as recited in claim 1, wherein the extensions are positioned between the arms and the second end of the second member.

15. An electro-surgical instrument as recited in claim 1, wherein a lower surface of the first member translates along a top surface of the second member as the first member moves relative to the second member along the longitudinal axis, the first member comprising an upper surface opposite the lower surface, and end surface of the first member being convexly curved from the upper surface to the lower surface, the end surface having a continuous radius of curvature., the first electrode being disposed on the end surface.

16. An electro-surgical instrument comprising:
    a first member extending along a longitudinal axis between a first end including spaced apart arms and an opposite second end having a first electrode; and
    a second member extending along the longitudinal axis between a first end having an elongated slot and an opposite second end having a second return electrode, the second ends defining a tissue cavity;
    an actuator comprising a handle arm that is integrally formed with the second end of the second member and a lever that is pivotable relative to the handle arm, the lever comprising spaced apart extensions, outer surfaces of the extensions engaging inner surfaces of the arms and an outer surface of the handle arm engaging inner surfaces of the extensions; and
    a first pin that extends through the arms of the first member, the extensions and the slot; and
    a second pin that extends through the handle arm and the extensions, the lever being pivotable about the second pin to translate the first pin within the slot along the longitudinal axis such that the first member translates relative to the second member along the longitudinal axis to selectively adjust a length of the cavity to orient the electrodes to ablate, cut and/or coagulate tissue.

17. An electro-surgical instrument as recited in claim 16, wherein the extensions are disposed between the arms of the lever and the handle arm as the lever pivots about the second pin.

18. An electro-surgical instrument as recited in claim 16, wherein the second pin is spaced apart from the first member.

19. An electro-surgical instrument as recited in claim 16, wherein the slot includes a first end and an opposite second end, the cavity having a first length when the first pin is positioned at the first end of the slot and an increased second length when the first pin is positioned at the second end of the slot.

20. An electro-surgical instrument comprising:
    a first member extending along a longitudinal axis between a first end including spaced apart arms and an opposite second end having a first electrode; and
    a second member extending along the longitudinal axis between a first end having an elongated slot and an opposite second end having a second return electrode, the second ends defining a tissue cavity;
    an actuator comprising a handle arm and a lever that is pivotable relative to the handle arm, the handle arm being fixed relative to the second member, the lever comprising spaced apart extensions, outer surfaces of the extensions engaging inner surfaces of the arms of the first member and the first member second end of the second member engaging inner surfaces of the extension;
    a first pin that extends through the arms of the first member, the slot and the lever; and a second pin that extends through the handle arm and the extensions, the lever being pivotable about the second pin to translate the first pin within the slot along the longitudinal axis such that the first member translates relative to the second member along the longitudinal axis to selectively adjust a length of the cavity to orient the electrodes to ablate, cut and/or coagulate tissue, wherein the extensions are disposed between the arms and the handle arm as the lever pivots about the second pin.

* * * * *

UNITED STATES PATENT AND TRADEMARK OFFICE
CERTIFICATE OF CORRECTION

PATENT NO. : 9,622,811 B2
APPLICATION NO. : 14/186019
DATED : April 18, 2017
INVENTOR(S) : Metcalf et al.

It is certified that error appears in the above-identified patent and that said Letters Patent is hereby corrected as shown below:

In the Claims

In Column 11, Line 22, in Claim 1, delete "first in" and insert -- first pin --, therefor.

In Column 12, Line 11, in Claim 15, delete "curvature.," and insert -- curvature, --, therefor.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*